Aug. 14, 1962 R. G. JELLY Plant Pat. 2,165
ROSE PLANT
Filed Sept. 29, 1961
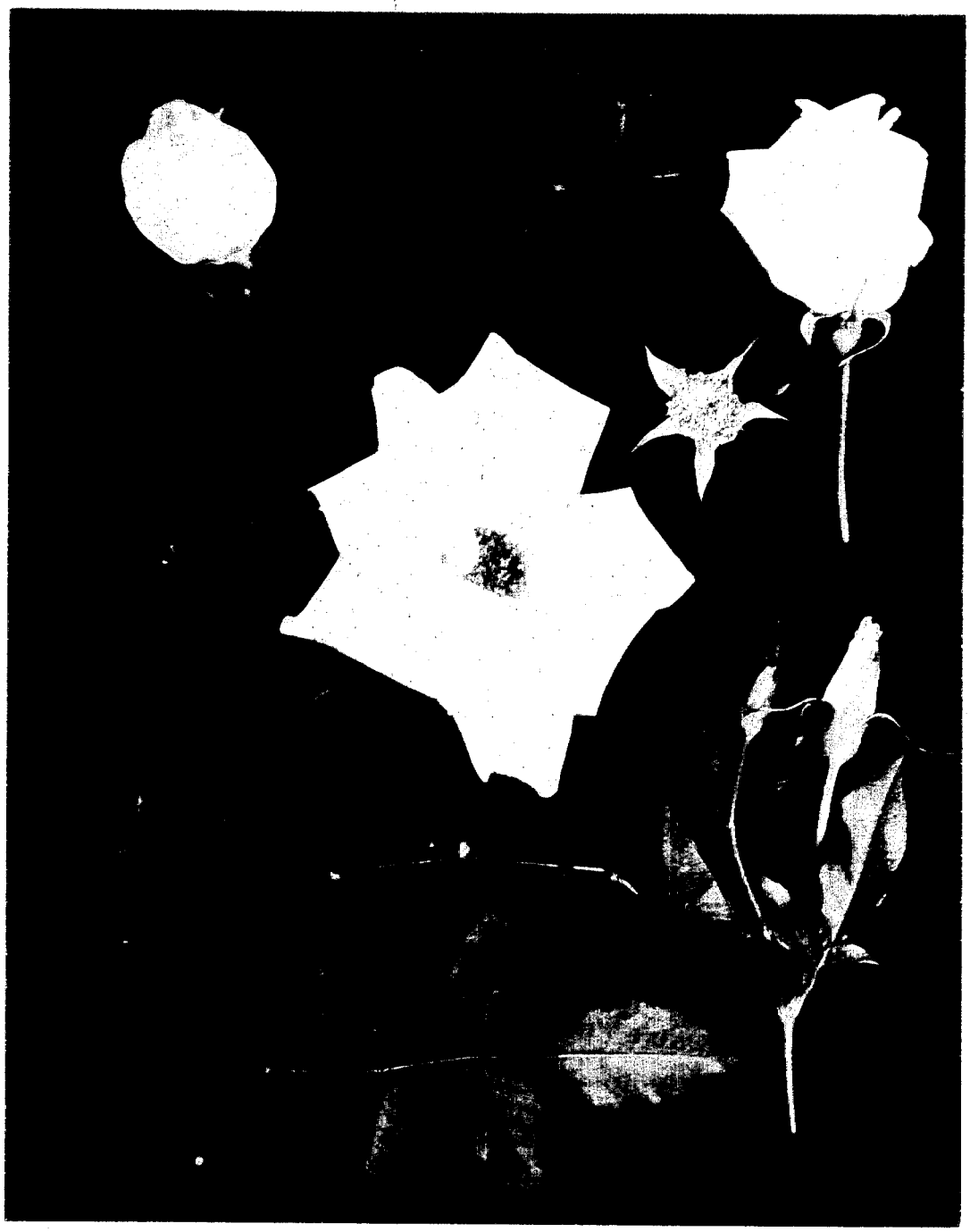
INVENTOR
Robert G. Jelly
BY Robb & Robb
ATTORNEYS United States Patent Office Plant Pat. 2,165
Patented Aug. 14, 1962

2,165
ROSE PLANT

Robert G. Jelly, Richmond, Ind., assignor to E. G. Hill Co., Inc., Richmond, Ind., a corporation of Indiana Filed Sept. 29, 1961, Ser. No. 141,924
1 Claim. (Cl. 47—61)

The present invention relates to a new and distinct variety of rose plant of the hybrid tea class, which was originated by me by crossing the variety "Snow White" (Plant Patent No. 348) with an unnamed and unpatented seedling of "Snow White."

The primary objective of this breeding was to produce a new rose variety from which there has been eliminated some of the faults of white rose varieties presently found in commercial floriculture. This objective was achieved in many respects, as evidenced by the following unique combination of characteristics which are outstanding in the new variety and which distinguish it from its parents, as well as from all other varieties of which I am aware:

(1) An upright habit of plant growth;
(2) Extremely attractive and glossy foliage;
(3) Good flower productivity;
(4) A high-centered and substantially perfect bud form;
(5) A distinctive and attractive white general color tonality of the flowers;
(6) Good petal texture; and
(7) Good keeping qualities of the flowers.

In comparison with its seed parent "Snow White," my new variety bears foliage which is much glossier, is more upright in its habit of growth, and bears more perfectly formed high-centered buds.

As compared with its unnamed seedling pollen parent, the new variety produces more flowers, the flowers have better keeping qualities, and the flower petals have better texture.

A sexual reproduction of the new variety by both grafting and budding, as performed at Richmond, Indiana, and at Livermore, California, shows that the foregoing characteristics and distinctions come true to form and are established and transmitted through succeeding propagations.

The accompanying drawing shows typical specimens of the vegetative growth and flowers of my new variety in different stages of development stages of development and as depicted in color as nearly true as it is reasonably possible to make the same in a color illustration of this character.

The following is a detailed description of the new variety, with color terminology in accordance with Robert Ridgway's Color Standards and Nomenclature (hereinafter abbreviated as "R") and Robert S. Wilson's Horticultural Colour Chart (hereinafter abbreviated as "W"), as indicated, except where general color terms of ordinary dictionary significance are obvious.

Type: Seedling; greenhouse; for cut flowers.
Class: Hybrid tea.
Breeding: Seedling.
*Seed parent.*—"Snow White."
*Pollen parent.*—An unnamed seedling of "Snow White."
Propagation: Holds its distinguishing characteristics through succeeding propagations by both grafting and budding.

*Flower*

Locality where grown and observed: Richmond, Indiana.
Flowers borne: Usually one to stem, but occasionally 2 or 3 (usually disbudded commercially to a single flower); on moderately strong stems of medium length.
Quantity of bloom: Free, in greenhouse.
Continuity: Continuous, in greenhouse.
Fragrance: Slight, in greenhouse. Nature—sweetbriar.
Bud:
*Peduncle.*—From short to medium length; medium diameter; erect; medium strong. Bark—entirely smooth; color—Lettuce Green, Plate V R. Thorns—none. Prickles—none. Hairs—none.
*Before calyx breaks.*—Size—medium large. Form—long pointed; without a conspicuous neck; with foliaceous appendages on the surface of the bud; with slender foliaceous parts extending beyond the tip of the bud equal to from ¼ to ½ of its length. Color—shaded from Spinach green, Plate 0960/1 W at edge to Scheeles Green, Plate 860/2 W at inside.
*As calyx breaks.*—Color—outside petal Pale Dull Green-Yellow, Plate XVII R, with slightly darker venation.
*As first pedal opens.*—Size—medium small. Form—long pointed. Color: outside—white, with base Pale Glass Green, Plate XXXI R, and with basal petal venation of Cosse Green, Plate V R; Inside—white, with base Pale Glass Green, Plate XXXI R, and with basal petal venation of Lettuce Green, Plate V R.
*Opening.*—Opens up fairly well in greenhouse; bud and bloom decrease in size during periods of high temperatures.
Bloom:
*Size (when fully open).*—Medium; from 4½ to 5½ inches.
*Petalage.*—Semi-double; from 18 to 24 petals; arranged regularly.
*Form.*—High centered at first, but becoming from high centered to globular; pedals being at first very tightly rolled inward, but becoming very loosely rolled later at maturity.
Petals:
*Texture.*—Moderately thick. Inside—satiny. Outside—from satiny to flat.
*Shape.*—Outer—from ovate to obovate, with apex flat, and with an occasional petal apex slightly emarginate. Intermediate—from oval to obovate, with apex acute to slightly cuspidate. Inner—from oval to obovate, with apex from acute to slightly emarginate.

This description of a newly opened flower was made from a rose grown in a greenhouse during the month of November at Richmond, Indiana:

*Color.*—Outer petal: outside surface—white, with base Primrose Yellow, Plate XXX R; inside surface—white, with base shaded from Primrose Yellow, Plate XXX R, to Strontian Yellow, Plate XVI R. Intermediate petal: outside surface—white, with base a shade lighter than Primrose Yellow, Plate XXX R; inside surface—white, with base Citron Yellow, Plate XVI R. Inner petal: outside surface—white, with base Sulphur Yellow, Plate V R; inside surface—white, with base Barium Yellow, Plate XVI R.

This description was made from a rose that was open for three days in a greenhouse during the month of April at Richmond, Indiana:

*Color.*—Outer petal: outside surface—white, with base Reed Yellow, Plate XXX R; inside surface—white, with base Citron Yellow, Plate XVI R. Intermediate petal: outside surface—white, with base shade lighter than Barium Yellow, Plate XVI R; inside surface—white, with base Strontian Yellow, Plate XVI R. Inner petal: outside surface—white, with base Naphthalene Yellow, Plate XVI R; inside surface—white, with base shaded from Martius Yellow, Plate IV R, to Pale Lemon Yellow, Plate IV R.

*General color effect.*—Newly opened flower—white, with base of petals from Martius Yellow, Plate IV R to Picric Yellow, Plate IV R. 3-days open—white, with base approaching Martius Yellow, Plate IV R.

*Behavior.*—Persist in greenhouse; bud must not be cut too tight for pure white colar; remains white until browning from age.

*Flower longevity.*—Cut flowers grown in greenhouse and kept at living room temperatures—6 days in November.

*Plant*

Foliage:

*Leaves.*—Compound of 3 to 5 leaflets; normal abundance; medium size; very glossy texture on current wood; becoming dull on older growth.

*Leaflets.*—Shape—Ovoid, with apex acute. Base—obtuse. Margin—serrate.

*Color.*—Mature: upper surface—very glossy and slightly than Empire Green, Plate XXXII R; under surface—slightly grayer than Bice Green, Plate XVII R. Young: upper surface—Frost Green, Plate XVII R; under surface—a shade lighter than Cedar Green, Plate 80 W.

*Rachis (the supporting stem of the compound leaf).*—Medium. Upper side—grooved and prickly at rim of groove. under side—a few thorns and prickles (thorns not being evident on all leaflets).

*Stipules.*—Medium length; medium width; with moderately short points turning out at an angle of less than 45° toward the stem.

Growth (in greenhouse):

*Habit.*—Upright; much-branched.

*Growth.*—Moderately free; vigorous.

*Canes.*—Medium diameter.

*Main stems.*—Color—Deep Dull Yellow-Green (1), Plate XXXII R. Thorns—few; medium length; usually straight, but some hooked downward to a slight degree; with short, ovoid base; color—slightly darker than Sayal Brown, Plate XXXIX R. Prickles—none. Hairs—none.

*Branches.*—Color—from Forest Green, Plate XVII R to slightly darker than Forest Green, Plate XVII R. Thorns—few; medium length; hooked slightly downward; with from short to medium base; color—from slightly lighter than Oil Yellow, Plate V R on younger branches to Sayal Brown, Plate XXXIX R on older branches. Prickles—none. Hairs—none.

*New shoots.*—Color—varies from Lettuce Green, Plate V R to Spinach Green, Plate V R. Thorns—very few; color—slightly darker than Oil Yellow, Plate V R. Prickles—none. Hairs—none.

*Reproductive Organs*

Stamens: Medium number; arranged about pistils, but with some mixed with petaloids.

Filaments: From short to medium length; most with anthers. Color—varies from Orange Buff, Plate 50 7/2 W to Cardinal Red, Plate 8 22/2 W, or one shaded with the other.

Anthers: Medium; open at various times. Color—Orange Buff, Plate 50 7/2 W, with an edging of Bay, Plate II R.

Pollen: From moderate to abundant. Color—from Cadmium Orange, Plate 8 W to Cadmium Orange, Plate 8/1 W.

Pistils: Medium number.

Styles: Fairly even; medium length; moderately thin; bunched. Color —shading from Martius Yelloy, Plate IV R at the base to Cardinal Red, Plate 8 22/2 W.

Stigma: Color—Apricot Yellow, Plate IV R.

Ovaries: Some protruding from calyx.

Hips: Medium length; ovoid; with inconspicuous neck; pear-shaped; smooth; walls fairly thin and fleshy.

Sepal: Permanent; medium length.

Seeds: Many; medium size.

I claim:

A new and distinct variety of rose plant of the hybrid tea class, substantially as herein shown and described, characterized particularly as to novelty by the unique combination of an upright habit of plant growth, extremely attractive and glossy foliage, good flower productivity, a high-centered and substantially perfect bud form, a distinctive and attractive white general color tonality of the flowers, good texture of the flower petals, and good keeping qualities of the flowers.

No references cited.